United States Patent [19]

El-Chahawi et al.

[11] Patent Number: 4,699,999

[45] Date of Patent: Oct. 13, 1987

[54] METHOD OF PREPARING PURE CARBOXYLIC ACIDS

[75] Inventors: Moustafa El-Chahawi; Günter Meyer, both of Troisdorf, Fed. Rep. of Germany

[73] Assignee: Dynamit Nobel AG, Cologne, Fed. Rep. of Germany

[21] Appl. No.: 894,733

[22] Filed: Aug. 8, 1986

Related U.S. Application Data

[63] Continuation of Ser. No. 675,770, Nov. 28, 1984, abandoned.

[30] Foreign Application Priority Data

Dec. 15, 1983 [DE] Fed. Rep. of Germany ....... 3345411

[51] Int. Cl.$^4$ .............................................. C07C 99/12
[52] U.S. Cl. .................................................. 562/450
[58] Field of Search .................... 562/406, 443, 450

[56] References Cited

U.S. PATENT DOCUMENTS

| | | | |
|---|---|---|---|
| 2,757,204 | 7/1956 | Ratcliff | 562/450 |
| 2,757,377 | 7/1956 | Mertzweiller et al. | 562/450 |
| 3,246,024 | 4/1966 | Gwynn et al. | 562/450 |
| 3,644,443 | 2/1972 | Shubkin | 562/406 |
| 3,766,266 | 10/1973 | Wakamatsu et al. | 562/406 |
| 3,996,288 | 12/1976 | Yukata et al. | 562/406 |
| 4,264,515 | 4/1981 | Stern et al. | 562/450 |
| 4,447,644 | 5/1984 | El Chahawi | 562/406 |
| 4,481,369 | 11/1984 | Walfram | 562/406 |
| 4,488,999 | 12/1984 | Feld | 562/414 |
| 4,490,298 | 12/1984 | Feld | 562/414 |

FOREIGN PATENT DOCUMENTS

| | | | |
|---|---|---|---|
| 2364039 | 7/1974 | Fed. Rep. of Germany | 562/406 |
| 1414910 | 11/1975 | United Kingdom | 562/443 |

OTHER PUBLICATIONS

Feld, Chem. Abst., vol. 99, #213,028w (1983).
Feld, Chem. Abst, vol. 99, #213029x (1983).
Packter et al, Chem. Abst, vol. 83, #85717a (1975).
New Syntheses with Carbon Monoxide, Ed. J. Falbe, Springer-Verlag, 1980, pp. 80–84 and 163.
Synthesen mit Kohlenmonoxyd, Ed. J. Falbe, Springer-Verlag, 1967, pp. 19 to 21.

*Primary Examiner*—James H. Reamer
*Attorney, Agent, or Firm*—Felfe & Lynch

[57] ABSTRACT

From reaction solutions of carboxylic acids prepared by carbonylation with the aid of cobalt carbonyl catalysts, the cobalt of the catalyst is precipitated by the addition of at least equivalent amounts of monocarboxylic or dicarboxylic acids and neutralization with alkaline agents, in the form of a cobalt(II) salt of the added acid, and the carboxylic acid is completely recovered from the reaction solution by acidification.

4 Claims, No Drawings

METHOD OF PREPARING PURE CARBOXYLIC ACIDS

This application is a continuation of application Ser. No. 675,770, filed Nov. 28, 1984, now abandoned.

BACKGROUND OF THE INVENTION

The invention relates to a method for preparing pure carboxylic acids from their reaction solutions, wherein cobalt carbonyl catalysts, such as especially $Co_2(CO)_8$ or corresponding ionic cobalt carbonyl compounds, are contained. Such cobalt carbonyl catalysts contain valuable cobalt, which it is desirable to recover. Furthermore, the cobalt catalysts make it difficult to produce the carboxylic acids in pure form and they form contaminants in the target products.

By known methods of carbonylation with cobalt carbonyl catalysts, especially dicobalt octacarbonyl, a series of carboxylic acids can be prepared by the insertion of one or, in some cases, two molecules of carbon monoxide and, if desired, additional molecular components, such as for example aryl acetic acids, especially phenylacetic acid, malonic acid and its esters, phenylpyruvic acid, and numerous others. In this case comparatively small amounts of the cobalt catalyst need to be separated.

In the case of the preparation of acetylaminocarboxylic acids, especially N-acetyl-DL-phenylalanine, however, very large amounts of cobalt carbonyl catalyst are required.

Especially, therefore, the invention relates to a method for preparing pure N-acetyl amino acids, including particularly N-acetyl-DL-phenylalanine, by the removal of cobalt carbonyl catalysts from the reaction solution while at the same time recovering the cobalt they contain.

N-acetyl amino carboxylic acids, especially N-acetylalpha-aminocarboxylic acids, can be obtained in a manner known in itself, described in German publication OS No. 2,364,039, from the corresponding organic halides by transposition with hydrogen and carbon monoxide in the presence of cobalt carbonyl catalysts and an amide. In this process large amounts of cobalt carbonyl catalysts are necessary. The German publication, however, specifies no technically useful method of selectively and completely removing the large amounts of the catalyst and recovering the cobalt. Furthermore, the German publication does not disclose how the acetyl aminocarboxylic acids are isolated and can be separated from the residues of the cobalt in the necessary manner. Accordingly, the method taught by the German publication is impractical in the disclosed form.

The problem existed of isolating carboxylic acids from their reaction solutions containing cobalt carbonyl catalysts, freeing them insofar as possible from residues of cobalt compounds, and recovering the cobalt contained in the cobalt carbonyl catalysts in a form which permits the reuse of the cobalt.

The problem consisted especially in preparing N-acetylalpha-aminocarboxylic acids, especially N-acetyl-DL-phenylalanine, in pure form with minimal losses from their reaction solutions containing cobalt carbonyl catalysts, separating the cobalt of the catalyst from the target product, removing it as completely as possible from the reaction solution, and isolating it in recoverable form.

This problem is aggravated by the requirement of high purity for the acetyl amino acids, especially insofar as they are to be used for pharmaceutical purposes, and especially again insofar as they are intended for use as starting substances for enzymatic deracemization. The problem is further aggravated by incomplete formation of the N-acetyl aminocarboxylic acid and by the large percentages of byproducts as well as large amounts of chlorides in the reaction solution.

THE INVENTION

It has been found that a high yield and a high purity are obtained in the N-acetyl aminocarboxylic acids, and especially in N-acetyl-DL-phenylalanine, and that degradation and transformation of the cobalt carbonyl catalyst in the reaction solution can be achieved, and cobalt can be precipitated as a salt of an added mono- or dicarboxylic acid. From the resulting solution of the target product, the carboxylic acid, especially N-acetyl-alpha-aminocarboxylic acid, and preferably N-acetyl-DL-phenylalanine, can be recovered in pure form with good yield. To this end it is proposed to transform the target product with bases to its salt form, and to precipitate it by acidification with concentrated acids, especially mineral acids, and isolate it.

The subject matter of the invention is therefore a method for the preparation of carboxylic acids in pure form from reaction solutions containing cobalt carbonyl catalysts, characterized by:

(a) adding monocarboxylic acids of 1 to 3 carbon atoms, dicarboxylic acids of 2 to 3 carbon atoms, or their aqueous solutions, in an amount at least equivalent to the cobalt of the catalyst, (b) neutralizing the reaction solution by the addition of alkaline substances and removing the cobalt salt of the acid added in accordance with a), and (c) working up the carboxylic acid from the reaction solution.

Also subject matter of the invention is a method for working up such reaction solutions, characterized by neutralizing the organic phase with alkaline agents, and then separating it from the aqueous phase which contains the target product.

Preferably, the target product is separated from the resultant aqueous phase by precipitating it with acids, especially mineral acids, and isolating it by separation.

Furthermore, and preferentially, it is very advantageous to recycle the separated organic phase in accordance with the invention to the production process. It is desirable for this purpose to distill the organic phase. In this manner the solvents used are again made available for the production of the carboxylic acid in question.

It has been found that the carboxylic acid that develops in the carbonylation, especially N-acetyl aminocarboxylic acids, and of these especially N-acetyl-DL-phenylalanine, whose content can be determined in the reaction solution by analysis, can be recovered virtually quantitatively by the present method of purification. Also very remarkable is the high purity of the target product, especially N-acetyl-DL-aminocarboxylic acids, of 98% or more. The product in question has virtually the theoretical acid number.

It has surprisingly been found that the cobalt can be removed from the zero-valence state in the organic phase of the reaction solution, and from the minus-one valence state the aqueous phase, in the form of a bivalent cobalt salt of the organic acid used for the precipitation, in a virtually quantitative manner.

Organic carboxylic acids, especially monocarboxylic acids of 1 to 3 carbon atoms, and of these especially the saturated monocarboxylic acids, as well as dicarboxylic acids of 2 to 3 carbon atoms, especially the saturated dicarboxylic acids, can be used for the precipitation. Preferred are formic acid and oxalic acid. Oxalic acid is greatly preferred.

The carboxylic acids used for the precipitation are to be used in an amount at least equivalent to the amount of cobalt in the catalyst, which can be determined by analysis. An excess of up to 20% more than the equivalent amount is desirable, preferably an excess of up to 10%. The acids used can be added as pure substances in liquid or solid form, or in the form of their aqueous solutions. Aqueous solutions are best added in greatly concentrated form. Addition to the hot reaction solution is possible. In general the addition will be performed at temperatures from 20° to 90° C., preferably at 50° to 80° C. After the addition of the monocarboxylic or dicarboxylic acids the reaction solution is preferably maintained at the addition temperature for up to one hour.

Then, by the addition of alkaline substances, i.e., an alkali hydroxide such as sodium hydroxide or potassium hydroxide, or alkali carbonates such as sodium carbonate, sodium bicarbonate or potassium carbonate, or by the addition of calcium hydroxide, preferably in concentrated aqueous solution, the reaction solution is adjusted to pH levels between 5.8 and 8, preferably 6.8 to 7.2.

The precipitating cobalt salt of the added monocarboxylic or dicarboxylic acid can then be removed, for example by filtration.

The filtration of the cobalt salt leaves an aqueous phase containing the salt of the carboxylic acid of the reaction solution—in the case of N-acetyl-alpha-aminocarboxylic acids the salts thereof—as well as an organic phase, especially containing solvents of the reaction solution used in the carbonylation, as well as any byproducts that may have formed.

It has been found that an excellent separation of the target product from the other substances can be achieved in this manner.

The separated aqueous phase can then be treated with concentrated acids, especially mineral acids such as hydrochloric acid, sulfuric acid or phosphoric acid, very preferably hydrochloric acid, for the complete precipitation of the carboxylic acid formed by carbonylation. The acidification is to be performed to pH 1. If necessary, cooling can be performed during or after the addition of the mineral acid. It has been found that a perfect separation of the carboxylic acid formed by carbonylation is possible. In particular, N-acetyl-alpha-aminocarboxylic acids, and of these especially N-acetyl-DL-phenylalanine, can be separated from the aqueous phase very completely, in a high purity and with extraordinarily low cobalt contents, by the addition of the acids.

In the following examples, the statement of the yields relates to the known preparation process described in German publication OS No. 2,364,039. By the purification measures of the invention, virtually 100% of the carboxylic acids that form are recovered. The precipitated cobalt salts can be transformed to the oxides, from which the cobalt carbonyl catalysts can be prepared in a known manner.

EXAMPLES

EXAMPLE 1

3.5 kg of benzyl chloride, 2.16 kg of acetamide, 1.72 kg of sodium hydrogen carbonate, 4 liters of water, 4 liters of methylisobutylketone and 8 kg of a 13 weight-percent solution of dicobalt octacarbonyl in methylisobutylketone are placed in an autoclave equipped with a stirrer. After the addition of a mixture of carbon monoxide and hydrogen gas (ratio 1:1 by volume) up to a pressure of 180 bar, the temperature is raised to 110° C. Beginning at a temperature of 80° C. a rapid absorption takes place. As soon as no further pressure drop occurs, the autoclave is cooled and the remaining carbon monoxide and hydrogen gas is let off. The reaction mixture is treated at 80° C. with 0.95 kg of oxalic acid dissolved in 10 liters of water. After one hour the suspension is cooled and neutralized with a 50 weight-percent soda lye (pH 7.0).

After filtration and drying, 1.1 kg of cobalt oxalate is obtained. Then the aqueous phase is separated from the filtrate and concentrated hydrochloric acid is added at a temperature between 50° and 80° C. to reach pH 1. After cooling, filtration and drying, 3.7 kg of N-acetyl-phenylalanine is obtained.

| | |
|---|---|
| GC purity approx. | 98% |
| Cobalt content | 40 ppm |
| Yield | 66.5%, i.e., virtually 100% of the acetyl phenylalanine that formed. |

The methylisobutylketone is separated from the separated organic phase by distillation, in a purity of more than 99% and reused in the reaction.

EXAMPLE 2

The reaction of Example 1 is repeated, but the cobalt of the catalyst is completely precipitated by using 1012 g of formic acid instead of oxalic acid. After cooling and drying, 696 g of cobalt formiate is obtained. After acidification as in Example 1, but with sulfuric acid, nearly 100% of the determined quantity of the N-acetyl-phenylalanine target product is obtained.

EXAMPLES 3 to 7

The procedure is similar to Example 1, but is performed with the addition of the following bases to achieve a pH of 7.0:

| Example | Base | Purity of the N—acetylphenylalanine |
|---|---|---|
| 1 | KOH | 98.0 |
| 4 | Na$_2$CO$_3$ | 99.2 |
| 5 | NaHCO$_3$ | 99.0 |
| 6 | LiOH | 97.5 |
| 7 | Ca(OH)$_2$ | 98.0 |

The cobalt is completely separated as oxalate, and the N-acetyl-phenylalanine is obtained virtually free of cobalt, in the above-listed high purity.

It will be understood that the specification and examples are illustrative but not limitative of the present invention and that other embodiments within the spirit and scope of the invention will suggest themselves to those skilled in the art.

We claim:

1. A method of producing N-acetyl-DL-phenylalanine carboxylic acid in pure form from a reaction solution containing a cobalt carbonyl catalyst comprising:
   (a) treating the reaction solution with oxalic acid or an aqueous solution thereof in an amount at least equivalent to the cobalt of the catalyst; (b) neutralizing the reaction solution by adding an alkaline substance and removing precipitated cobalt oxalate; and (c) working up the carboxylic acid from the reaction solution.

2. The method of claim 1 wherein, after neutralization, said reaction solution is separated into an organic and an aqueous phase for the working up of the carboxylic acid from the reaction solution.

3. The method of claim 2, wherein the carboxylic acid is precipitated from the aqueous phase by acidification and isolated.

4. The method of claim 3, wherein the separated organic phase is returned to the preparation process.